United States Patent
Franz

(10) Patent No.: US 8,718,788 B2
(45) Date of Patent: *May 6, 2014

(54) NOTCHED ELECTRODE FOR ELECTROSTIMULATION LEAD

(75) Inventor: Brian Franz, Flower Mound, TX (US)

(73) Assignee: Advanced Neuromodulation Systems, Inc., Plano, TX (US)

(*) Notice: Subject to any disclaimer, the term of this patent is extended or adjusted under 35 U.S.C. 154(b) by 298 days.

This patent is subject to a terminal disclaimer.

(21) Appl. No.: 13/240,497

(22) Filed: Sep. 22, 2011

(65) Prior Publication Data

US 2012/0010671 A1    Jan. 12, 2012

Related U.S. Application Data

(63) Continuation of application No. 12/367,849, filed on Feb. 9, 2009, now Pat. No. 8,036,755, which is a continuation of application No. 11/143,160, filed on Jun. 2, 2005, now Pat. No. 7,489,971.

(60) Provisional application No. 60/577,311, filed on Jun. 5, 2004.

(51) Int. Cl.
*A61N 1/05* (2006.01)

(52) U.S. Cl.
CPC .................... *A61N 1/0551* (2013.01)
USPC ....................................................... 607/116

(58) Field of Classification Search
CPC ...................................................... A61N 1/0551

USPC ............................................................ 607/116
See application file for complete search history.

(56) References Cited

U.S. PATENT DOCUMENTS

| | | | |
|---|---|---|---|
| 4,442,846 A | 4/1984 | Brighton et al. | |
| 4,738,812 A | 4/1988 | Raynal | |
| 4,913,164 A | 4/1990 | Greene et al. | |
| 5,199,443 A | 4/1993 | Maurer et al. | |
| 5,400,784 A | 3/1995 | Durand et al. | |
| 5,458,629 A | 10/1995 | Baudino et al. | |
| 5,516,396 A | 5/1996 | Maurer et al. | |
| 5,957,965 A | 9/1999 | Moumane et al. | |
| 6,032,061 A | 2/2000 | Koblish | |
| 6,181,971 B1 | 1/2001 | Doan | |
| 6,185,463 B1 * | 2/2001 | Baudino | 607/119 |
| 6,216,045 B1 | 4/2001 | Black et al. | |
| 6,405,067 B1 | 6/2002 | Mest et al. | |
| 6,430,425 B1 * | 8/2002 | Bisping | 600/374 |
| 6,430,442 B1 | 8/2002 | Peters et al. | |
| 6,456,886 B1 | 9/2002 | Howard, III et al. | |
| 6,456,888 B1 | 9/2002 | Skinner et al. | |
| 6,493,590 B1 | 12/2002 | Wessman et al. | |
| 6,526,321 B1 | 2/2003 | Spehr | |
| 7,489,971 B1 | 2/2009 | Franz | |
| 2002/0183817 A1 | 12/2002 | Van Venrooij et al. | |
| 2004/0015221 A1 | 1/2004 | Kuzma | |
| 2004/0093051 A1 | 5/2004 | Chinn et al. | |
| 2004/0098074 A1 | 5/2004 | Erickson et al. | |
| 2009/0143845 A1 | 6/2009 | Franz | |

* cited by examiner

Primary Examiner — Eric D. Bertram

(57) ABSTRACT

According to one embodiment, an electrode for use in electrostimulation is provided, where the electrode comprises a notch that operates to substantially eliminate gaseous material from being trapped about the electrode during a molding process of an electrostimulation lead.

20 Claims, 2 Drawing Sheets

NOTCHED ELECTRODE FOR ELECTROSTIMULATION LEAD

CROSS-REFERENCE TO RELATED APPLICATIONS

This application is a continuation of U.S. application Ser. No. 12/367,849, filed Feb. 9, 2009, now U.S. Pat. No. 8,036,755, which is a continuation of U.S. application Ser. No. 11/143,160, filed Jun. 2, 2005, now U.S. Pat. No. 7,489,971, which claims the benefit of U.S. Provisional Application No. 60/577,311, filed Jun. 5, 2004, the disclosures of which are incorporated herein by reference. This application is related to U.S. patent application Ser. No. 10/872,271, filed Jun. 18, 2004, now abandoned; and U.S. patent application Ser. No. 10/872,277, filed Jun. 18, 2004, now U.S. Pat. No. 7,346,395, the disclosures of which are hereby incorporated herein by reference.

TECHNICAL FIELD

This invention relates generally to the field of electrostimulation technology and more specifically to notched electrodes for use in an electrostimulation lead.

BACKGROUND OF THE INVENTION

Electrostimulation systems are designed to treat neurological disorders and for management of chronic pain. A typical electrostimulation system involves the use of a generator and a stimulation lead having a plurality of electrodes. The generator is coupled to the stimulation lead in order for the electrodes to provide low level electrical impulses that the stimulation lead applies to the treatment area. For example, the stimulation lead may be implanted in the epidural area of the body, where the electrical impulses stimulate targeted nerves. The stimulation may result in the brain replacing the sensation of pain with a more pleasing sensation called paresthesia.

For deep brain stimulation (DBS), the stimulation leads used for spinal cord stimulation (SCS) may not be adequately sized. A smaller stimulation lead, and correspondingly smaller electrodes, may be desired. However, providing such a smaller stimulation lead has posed some challenges in that merely resizing lead technology used for SCS has proven ineffective to provide a smaller stimulation lead, such as one useful for DBS, having desirable functional and aesthetic attributes. For example, according to one technique for providing a stimulation lead for use in SCS, a mold is used to manufacture the stimulation lead where the electrodes are placed in the mold, wires are soldered, or otherwise attached to the electrodes, and a fill material is injected into the mold. Injecting the material has posed some challenges because the volume of the lead is reduced and therefore air, vapor, or other gaseous material may become more easily trapped.

One technique for reducing or eliminating the trapped gaseous material involves injecting the fill material at higher pressure. The high pressure may result in the gas being pushed out of the mold before the fill material cures. This technique, however, may result in the weakening and/or detachment of wire contacts coupled to the electrode. Another technique may involve heating the fill material to decrease its viscosity in order to more easily fill the areas where gas may be trapped. This technique, however, may result in the discoloration of the material due to the increased temperatures, which is aesthetically unappealing. Additionally, heating the fill material may result in a change of the chemical properties of the resulting lead, which is unacceptable considering the need for bio-compatibility of the stimulation lead and the human body. Consequently, a need exists in the art for other techniques for removing gases.

BRIEF SUMMARY OF THE INVENTION

The present invention is directed to systems and methods which provide a notched electrode for use in electrostimulation. The notched electrode, of embodiments is operable to substantially eliminate gaseous material from being trapped about the electrode during the molding process of an electrostimulation lead or other stimulation portion body.

According to one embodiment, an electrode is a substantially circular band that is notched at either end, or both ends, of the band. The notch may have any depth, shape, size, configuration, and placement on the band according to various embodiments of the invention. In one instance, an electrode may have four notches, two at each end of the band. In another instance, the electrode may have eight notches, four at each end of the band. However, the notched electrode may include any suitable number of notches.

The notch may facilitate the elimination of trapped gas about the electrode during fabrication of a stimulation lead. The notch may also be used for other purposes, such as by providing a view, or "window", to enable monitoring if the electrode is filled during the injection step of fabricating a stimulation lead. For example, the notch may be placed on the electrode such that when the fill material occupies the notched area, the injection process monitoring the fill level may detect that the mold for a stimulation lead is completely filled.

Certain embodiments of the invention may provide one or more technical advantages. A technical advantage of one embodiment may be that the notch allows for trapped gas to escape during the injection process of fabricating a stimulation lead or other stimulation portion body such that heating the fill material at a high temperature that causes discoloration is not necessary. Another technical advantage of one embodiment may be that the stimulation portion mold may be resized and reshaped without having to redesign it for allowing trapped gas to escape during the injection process. Yet another technical advantage of one embodiment may be that the notch may be designed having any suitable dimension and shape to produce any aesthetic result desired. Additionally, having a notched electrode at the end of a stimulation portion body may result in the reduction of parts and materials needed to manufacture the stimulation portion body since a window piece may be eliminated.

The foregoing has outlined rather broadly the features and technical advantages of the present invention in order that the detailed description of the invention that follows may be better understood. Additional features and advantages of the invention will be described hereinafter which form the subject of the claims of the invention. It should be appreciated that the conception and specific embodiment disclosed may be readily utilized as a basis for modifying or designing other structures for carrying out the same purposes of the present invention. It should also be realized that such equivalent constructions do not depart from the invention as set forth in the appended claims. The novel features which are believed to be characteristic of the invention, both as to its design and method of fabrication, together with further objects and advantages will be better understood from the following description when considered in connection with the accompanying figures. It is to be expressly understood, however, that each of the figures is provided for the purpose of illustration and description only and is not intended as a definition of the limits of the present invention.

BRIEF DESCRIPTION OF THE DRAWINGS

For a more complete understanding of the present invention, reference is now made to the following descriptions taken in conjunction with the accompanying drawing, in which.

DETAILED DESCRIPTION OF THE INVENTION

Figure 1:
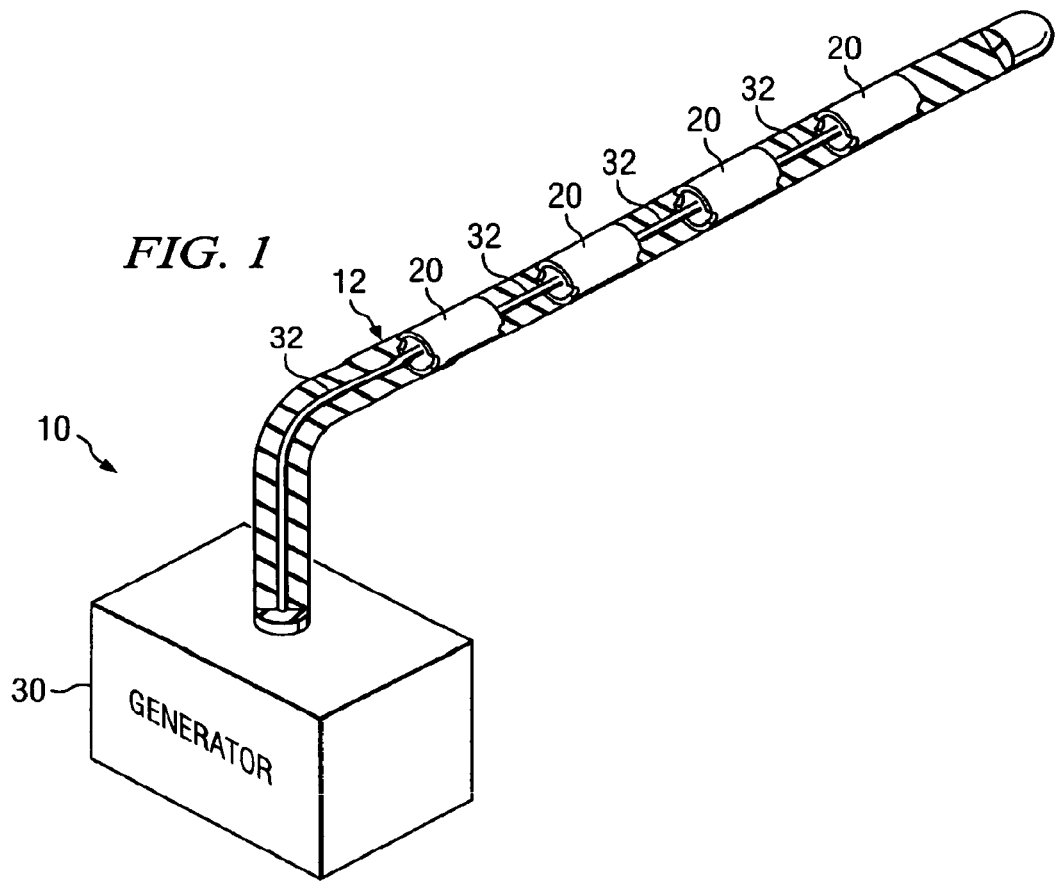
FIG. 1 is a diagram illustrating an example of an electrostimulation system using notched electrodes according to an embodiment of the present invention.

Directing attention to FIG. 1, an electrostimulation system 10 using electrodes 20 in a stimulation portion, such as lead 12, is shown. Electrostimulation system 10 includes a generator portion, shown as generator 30, and stimulation portion, shown as lead 12, that are used to deliver electrical impulses to nerves in a particular area of the human body. Typically, stimulation lead 12 is implanted near the targeted nerves and is coupled to generator 30. Generator 30 generates the electrical impulses, which pass through wires 32 to each electrode 20. Stimulation lead 12 includes at least one notched electrode 20 located near the end of stimulation lead 12 as shown. Stimulation lead 12 may include, however, more notched electrodes 20 without departing from the scope of the invention. According to one embodiment, the electrode 20 that is located at the end closest to generator 30 is referred to as the terminal end electrode, and the electrode 20 that is closest to the free end of stimulation lead 12 is referred to as the stimulation end electrode. The terminal end electrode and the stimulation end electrode may include a notch according to the teachings of the present invention. The terminal end electrode and the stimulation end electrode, however, may have different design and configurations from other electrodes 20, for example, these electrode may not be notched, may be threaded or otherwise adapted to accept a mating component such as a pull relief or tip, etcetera.

According to one embodiment, a mold is used to fabricate stimulation lead 12 having at least one notched electrode 20 that ensures a complete or substantially complete fill of the mold with a resilient material forming the body of lead 12, enclosing wires 32, and filling the spaces between electrodes 20. Accordingly, air, gas, vapor, or any other gaseous material that may become trapped during fabrication is substantially eliminated through the use of notched electrodes 20. Before injecting the mold with the fill material, electrodes 20 may be coupled to wires 32 in order to receive the electrical impulses from generator 30. The fill material may comprise a resin such as polyurethane. Any other suitable material may be used as fill material. Specifically, any other suitable bio-compatible material may be used as fill material according to embodiments of the invention. According to one embodiment, electrode 20 is made out of a platinum material. For example, electrode 20 may comprise ninety percent platinum and ten percent iridium. Electrode 20 of various embodiments may comprise any other suitable compound without departing from the scope of the invention.

The fill material of embodiments is injected to the mold using sufficient pressure to prevent the shearing of wires 32 and to allow for the fill material to press air out of the mold and to occupy the space inside and between each electrode 20. Air, or any other gaseous material, may become trapped under electrode 20 during this process. The notches are a means to facilitate the substantial elimination of gaseous material. The notch also facilitates filling an inside cavity of each electrode 20, which increases the pull strength associated with stimulation lead 12. Additionally, the notch may be used to provide a coupling area for wires 32. In other words, wires 32 may be welded inside the notch cavity so as to reduce the contact that wires 32 may have with the mold during the injection process. By welding wires 32 to the inside cavity of a notch, the shearing off of wires 32 during injection of the mold may be reduced or eliminated. Examples of embodiments of a notched electrode 20 will be described with reference to FIGS. 2-5.

Providing at least one notch at each electrode 20 may result in a fabrication process of stimulation lead 12 that reduces or substantially eliminates vapor lock. Additionally, a lower injection pressure may be used to inject the fill material in the mold used to form stimulation lead 12, thereby ensuring that the wire contact between wires 32 and electrodes 20 does not weaken or become detached. Other technical advantages may become apparent to one of ordinary skill in the art. For example, heating the fill material may be unnecessary thereby reducing the possibility of affecting the chemical properties of the materials composing stimulation lead 12. As yet another example, the mold used to form stimulation lead 12 may be resized to achieve the desired width and length without having to substantially redesign other parameters of the mold or pieces for the sole purpose of eliminating trapped gaseous material.

Figure 2:
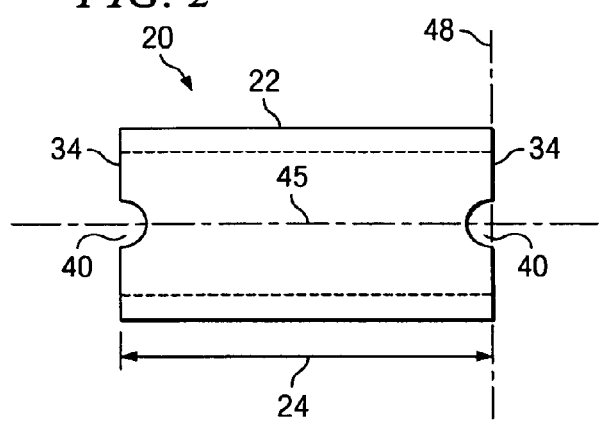
FIG. 2 is a diagram illustrating a side view of one embodiment of a notched electrode that may be used with a stimulation lead according to the present invention.

Turning now to FIG. 2, a side view of an embodiment of electrode 20 is shown. According to the illustrated embodiment, electrode 20 comprises a body portion 22 that may be formed in a cylindrical shape. Any other suitable shape may be used as body portion 22 without departing from the scope of the invention. Body portion 22 has a length 24, which in one embodiment comprises 0.060±0.001 inches in length. In another embodiment, length 24 comprises 0.118" inches in length. Length 24 may comprise any other suitable length without departing from the scope of the invention.

Notches 40 are located at opposite ends 34 of body portion 22. Notch 40 is shown as having a concave shape with a radius that may be selected using various criteria. In one embodiment, the sum of the radiuses of notches 40 may be selected to not exceed about one third of the overall length 24. For example, a length 24 comprising 0.60 inches results in the sum of radiuses of notches 40 to equal about 0.02 inches. According to the illustrated embodiment, each notch 40 comprises a radiused portion having a radius of 0.008±0.002 inches. Notch 40, however, may have any other suitable radius and shape without departing from the scope of the invention. For example, the radius of notch 40 may be smaller or larger depending on the effect desired. To illustrate the preceding example, notch 40 may be sized with a radius and/or shape that substantially avoids increasing the current density associated with the electrode and/or avoids points, or sharp edges, that may be associated with high current density and high heat concentration.

Although notches 40 are illustrated as being aligned with one another at ends 34, each pair of notches 40 may be located independently from the pair of notches 40 of the opposite end 34. The present embodiment shows at each end 34 at least one notch 40, where the center of each notch 40 is substantially aligned along central axis 45. However, each pair of notches 40 may be located at body portion 22 independently of each other so that the center of each notch 40 is not substantially aligned along the central axis 45. For example, one pair of notches 40 at one end 34 may be aligned along a perpendicular axis 48, while another pair of notches 40 at the other end 34 may be aligned along central axis 45. Any other suitable location for each pair of notches 40 may be used without departing from the scope of the invention.

Figure 3:
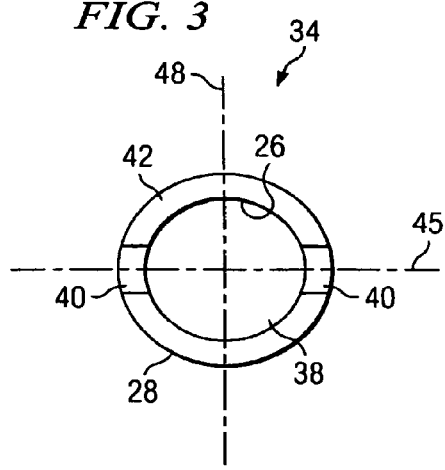
FIG. 3 is a diagram illustrating an end view of the embodiment shown in FIG. 2.

FIG. 3 is a diagram illustrating an end view of the embodiment shown in FIG. 2. Electrode 20 may include four notches 40 that substantially eliminate gaseous material from being trapped about electrode 20 during a molding process of stimulation lead 12. In the present embodiment, each end 34 comprises two notches 40 and the centers of notches 40 are substantially aligned with central axis 45.

Body portion 22 comprises a cylindrical band 42 and a central orifice 38. In the present embodiment, cylindrical band 42 comprises an inside diameter 26 of 0.045±0.0005 inches and an outside diameter 28 of 0.0600±0.0005 inches. Cylindrical band 42 may comprise any other suitable dimension. For example, stimulation lead 12 may be resized to accommodate applications that may need a larger or smaller thickness resulting in the need for a larger or smaller electrode 20. Although cylindrical band 42 is described and illustrated as being substantially cylindrical, other suitable shapes may be used without departing from the scope of the present invention.

According to the illustrated embodiment, central orifice 38 is a cylindrical area surrounded by the notched cylindrical band 42. Central orifice 38 may be used for passing through wires 32. Additionally, central orifice 38 may be filled with fill material during injection of the mold associated with stimulation lead 12. It is important to note that notches 40 may assist the injection process by providing a way to verify that central orifice 38 has been filled with fill material. Although the term "fill" is used, filling central orifice 38 may involve any other suitable process that ensures that a substantial portion of central orifice 38 is occupied by materials other than gaseous material. According to another embodiment (not shown), the inside surface of the cylindrical band 42 may be threaded to facilitate coupling with other parts of electrostimulation system 10 and to provide additional pull strength of stimulation lead 12. In the preceding example, the terminal end electrode and the stimulation end electrode may be notched on only one end 34 and may be threaded in order to accommodate a stylette guide equipped with a "window" that allows for degassing, as well as providing a visual reference that electrode 20 is completely filled underneath the threaded contact.

Figure 4:
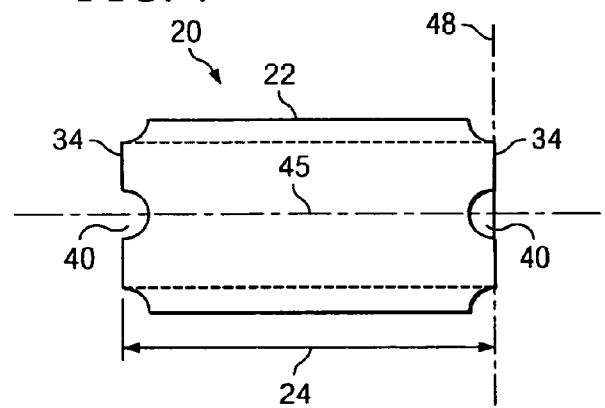
FIG. 4 is a diagram illustrating a side view of another embodiment of a notched electrode that may be used with a stimulation lead according to the present invention.

Turning now to FIG. 4, a side view of an embodiment of electrode 20 comprising eight notches 40 is shown. Electrode 20 in the present embodiment may comprise substantially the same dimensions than the electrode 20 illustrated at FIGS. 2 and 3. According to the present embodiment, electrode 20 comprises length 24 of 0.060±0.001 inches and a radius of notch 40 of 0.008±0.002 inches. Again, electrode 20 may have any other suitable dimension, for example, the radius of notch 40 may be larger or smaller, and length 24 may be longer or shorter without departing from the scope of the invention.

Notches 40 are located at opposite ends 34 of body portion 22. The present embodiment of electrode 20 includes eight notches 40. Four notches 40 at one side 34 and four notches 40 at the other side 34. In the present embodiment, one pair of notches 40 at one end 34 is aligned with another pair of notches 40 at the other end 34. That is, along the side of body portion 22, the center of a notch 40 at one end 34 and the center of another notch 40 at the opposite end 34 are substantially aligned along a central axis 45. Although the alignment may be ideal for aesthetic purposes, it is not a critical requirement of the present invention. For example, notches 40 at one end 34 of electrode 20 may not be aligned with notches 40 at the other end 34 of electrode 20.

Figure 5:
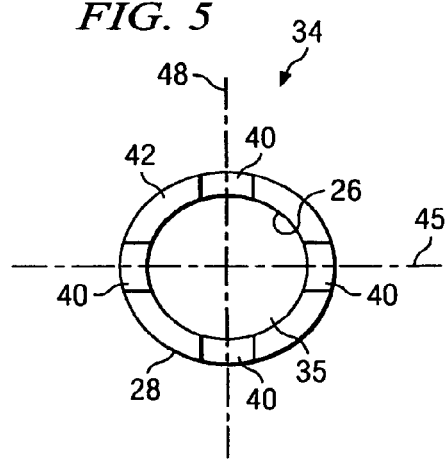
FIG. 5 is a diagram illustrating an end view of the embodiment shown in FIG. 4.

FIG. 5 is a diagram illustrating an end view of the embodiment shown in FIG. 4. Electrode 20 includes eight notches 40 that substantially eliminate gaseous material from being trapped about electrode 20 during the molding process of stimulation lead 12. In the present embodiment, each end 34 comprises four notches 40. One pair of notches 40 has centers substantially aligned with a central axis 45, while another pair of notches 40 has centers substantially aligned with a perpendicular axis 48. Each pair of notches 40 may be aligned along any other suitable axis. For example, instead of perpendicular axis 48 an axis being at sixty degrees with reference to central axis 45 may be used to align one pair of notches 40. Any other suitable axis may be used without departing from the scope of the invention.

As was described with reference to FIG. 3, cylindrical band 42 comprises an inside diameter 26 of 0.045±0.0005 inches and an outside diameter 28 of 0.0600±0.0005 inches. Cylindrical band 42 may, however, comprise any other suitable dimensions. For example, stimulation lead 12 may be resized to accommodate applications that may need a larger or smaller thickness resulting in the need for a larger or smaller electrode 20. Although cylindrical band 42 is described and illustrated as being substantially cylindrical, other suitable shapes may be used without departing from the scope of the present invention.

As was described with reference to FIG. 3, central orifice 38 is the cylindrical area surrounded by the notched cylindrical band 42. Central orifice 38 may be used for passing through wires 32. Additionally, central orifice 38 may be filled with fill material during injection of the mold associated with stimulation lead 12. It is important to note that during notches 40 may assist the injection process by providing a way to verify that central orifice 38 has been filled with fill material. Although the term "fill" is used, filling central orifice 38 may involve any other suitable process that ensures that a substantial portion of central orifice 38 is occupied by materials other than gaseous material. According to another embodiment (not shown), the inside surface of the cylindrical band 42 may be threaded to facilitate coupling with other parts of electrostimulation system 10 and to provide additional pull strength of stimulation lead 12.

Figure 6:
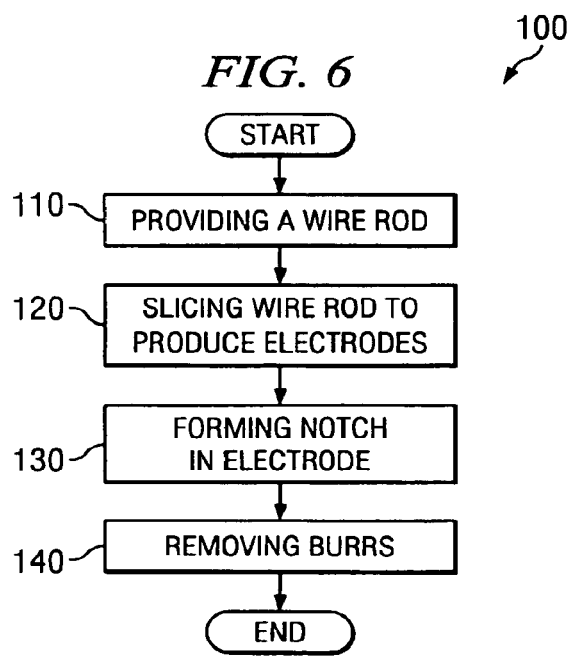
FIG. 6 is a flowchart demonstrating one embodiment of a method for manufacturing a notched electrode for use in electrostimulation according to the present invention.

FIG. 6 is a flowchart demonstrating one embodiment of a method 100 for manufacturing electrode 20 for use in electrostimulation according to the present invention. The method begins at step 110 where a wire rod is provided. The wire rod may be a tube made out of a platinum material. According to one embodiment, the platinum material may comprise ninety percent platinum and ten percent iridium. The wire rod may comprise an outside diameter of 0.0600±0.0005 inches and an inside diameter of 0.0450±0.0005 inches. Any other suitable dimensions may be used. For example, if a smaller electrode 20 is desired, a smaller outside diameter and inside diameter may be fashioned and the wire rod may be dimensioned accordingly.

At step 120, the wire rod is sliced to produce electrodes. The wire rod may be sliced at intervals corresponding to length 24. For example, the wire rod may be sliced every 0.060±0.001 inches to produce electrodes 20. Any suitable tool may be used to slice the wire rod as long as the precision of length 24 is preserved.

Notch 40 of electrode 20 is formed at step 130. According to one embodiment, four notches 40 are formed, two notches 40 at each side 34 of electrode 20. According to another embodiment, eight notches 40 are formed, four notches 40 at each side 34. The placement of notches 40 was described according to the particular descriptions of each embodiment as was referenced in FIGS. 2 through 5. A wire electrical discharge machine may be used to form the concave shape of notches 40. Any other suitable tool, however, may be used to form notches 40 without departing from the scope of the invention. Additionally, even though notches 40 are described as having a concave shape with a particular radius, notches 40 may comprise any other suitable shape without departing from the scope of the invention. For example, a notch 40 having a shallow curve resulting in less of a sharp edge between the ridge of the notch 40 and the surface of end 34 may be used.

At step 140 each electrode 20 may be processed to remove burrs. According to one embodiment, after forming notches 40, each electrode 20 is tumbled to remove burrs that may have resulted from slicing and/or forming notches 40. Any suitable process may be used to remove burrs without departing from the scope of the invention. After removing burrs at step 140 the method terminates.

Method 100 for manufacturing electrodes 20 may modified, such as by omitting or adding steps or performing the steps in any suitable order, without departing from the scope of the invention. For example, slicing the wire rod to produce electrodes at step 120 may be performed after forming notches 40 in the electrodes at step 130. Step 130 may in turn be modified to include boring orifices in the wire rod at intervals where the notches are to be located. In this example, an interval may be substantially the same length as the length of body portion 22. Additionally, the orifice may have a circular shape having a diameter substantially equal to twice the radius dimension of notch 40. Therefore, in this scenario, the center of each orifice may each be aligned with the slice line in order for each half of the orifice to form at least one notch 40. Any suitable tools may be used to bore the orifices and any other suitable process may be used to locate the orifices and slice notched electrodes 40.

Although the present invention and its advantages have been described in detail, it should be understood that various changes, substitutions and alterations can be made herein without departing from the invention as defined by the appended claims. Moreover, the scope of the present application is not intended to be limited to the particular embodiments of the process, machine, manufacture, composition of matter, means, methods and steps described in the specification. As one will readily appreciate from the disclosure, processes, machines, manufacture, compositions of matter, means, methods, or steps, presently existing or later to be developed that perform substantially the same function or achieve substantially the same result as the corresponding embodiments described herein may be utilized. Accordingly, the appended claims are intended to include within their scope such processes, machines, manufacture, compositions of matter, means, methods, or steps.

What is claimed is:

1. A method for fabricating a neurostimulation lead, comprising:
   providing a lead body comprising a plurality of conductor wires;
   providing a plurality of substantially cylindrical electrodes at a distal end of the lead body, wherein each electrode comprises a first peripheral edge at a first end of the respective electrode and a second peripheral edge at a second end of the respective electrode, wherein a plurality of notches are provided in each electrode circumferentially about the first peripheral edge;
   placing at least the distal end of the lead body with the plurality of electrodes into a mold; and
   injecting insulative material into the mold, wherein subsequent to the injection of insulative material, the plurality of notches facilitate the elimination of gaseous material from the insulative material promximate the corresponding electrode.

2. The method of claim 1 wherein the plurality of electrodes comprises four electrodes.

3. The method of claim 1 wherein the plurality of notches of each electrode are aligned circumferentially about the first peripheral edges.

4. The method of claim 1 wherein the insulative material is a polyurethane material.

5. The method of claim 1 wherein at least one of the plurality of notches possess a radius of curvature.

6. The method of claim 5 wherein a ratio between a length of each electrode and the radius of curvature of the first and second plurality of notches is approximately 0.60 inches/0.02 inches.

7. The method of claim 5 wherein the plurality of electrodes posses an outside diameter of approximately 0.06 inches.

8. A method for fabricating a neurostimulation lead, comprising:
   providing a lead body comprising a plurality of conductor wires;
   providing a plurality of substantially cylindrical electrodes at a distal end of the lead body, wherein each electrode comprises a first peripheral edge at a first end of the respective electrode and a second peripheral edge at a second end of the respective electrode, a plurality of notches are provided in each one of the electrodes circumferentially about at least one of the first peripheral edge and the second peripheral edge;
   placing at least the distal end of the lead body with the plurality of electrodes into a mold; and
   injecting insulative material into the mold, wherein subsequent to the injection of insulative material, the plurality of notches facilitate the elimination of gaseous material from the insulative material promximate the corresponding electrode.

9. The method of claim 8 wherein the plurality of electrodes comprises four electrodes.

10. The method of claim 8 wherein the plurality of notches of each electrode are aligned circumferentially about the peripheral edges.

11. The method of claim 8 wherein the insulative material is a polyurethane material.

12. The method of claim 8 wherein at least one of the plurality of notches possess a radius of curvature.

13. The method of claim 12 wherein a ratio between a length of each electrode and the radius of curvature of the first and second plurality of notches is approximately 0.60 inches/ 0.02 inches.

14. The method of claim 13 wherein the plurality of electrodes posses an outside diameter of approximately 0.06 inches.

15. A method for fabricating a neurostimulation lead, comprising:
- providing a lead body comprising a plurality of conductor wires;
- providing a plurality electrodes at a distal end of the lead body, wherein each electrode comprises a first peripheral edge at a first end of the respective electrode and a second peripheral edge at a second end of the respective electrode, wherein a at least one notch is provided in at least one of the plurality of electrodes circumferentially about at least one of the first peripheral edge and the second peripheral edge;
- placing at least the distal end of the lead body with the plurality of electrodes into a mold; and
- injecting insulative material into the mold, wherein subsequent to the injection of insulative material, the ate least one notch facilitates the elimination of gaseous material from the insulative material promximate the corresponding electrode.

16. The method of claim 15 wherein at least a second notch is provided in the at least one of the plurality of electrodes about at least one of the first peripheral edge and the second peripheral edge.

17. The method of claim 16 wherein the plurality of electrodes comprises four electrodes.

18. The method of claim 16 wherein the first notch and the second notch are aligned circumferentially about the peripheral edges.

19. The method of claim 16 wherein at least one of the first and second notches posses a radius of curvature.

20. The method of claim 15 wherein the insulative material is a polyurethane material.

\* \* \* \* \*